United States Patent [19]

Krekeler et al.

[11] 4,024,196
[45] May 17, 1977

[54] PROCESS FOR THE MANUFACTURE OF HYDROQUINONE

[75] Inventors: Hans Krekeler, Wiesbaden; Werner Heinrich Müller, Kelkheim, Taunus, both of Germany

[73] Assignee: Hoechst Aktiengesellschaft, Frankfurt am Main, Germany

[22] Filed: Aug. 5, 1975

[21] Appl. No.: 602,029

[30] Foreign Application Priority Data

Aug. 7, 1974 Germany .......................... 2437929

[52] U.S. Cl. .......................................... 260/621 H
[51] Int. Cl.² ........................................ C07C 39/08
[58] Field of Search ............ 260/621 H, 625, 621 R

[56] References Cited

UNITED STATES PATENTS

| | | | |
|---|---|---|---|
| 2,229,573 | 1/1941 | Jung | 260/621 H |
| 3,534,110 | 10/1970 | Juguin et al. | 260/621 H |
| 3,801,651 | 4/1974 | Adolphen | 260/613 D |
| 3,865,884 | 2/1975 | Agusto | 260/621 H |

Primary Examiner—James O. Thomas, Jr.
Assistant Examiner—W. B. Lone
Attorney, Agent, or Firm—Curtis, Morris & Safford

[57] ABSTRACT

The present invention is related to a process for the manufacture of hydroquinone by catalytic dehydrogenation of cyclohexanedione-(1,4) in the liquid phase by means of a dehydrogenation mixture composed of a solvent and a catalyst comprising a noble metal of Group VIII of the periodical system.

8 Claims, No Drawings

PROCESS FOR THE MANUFACTURE OF HYDROQUINONE

The present invention is related to a process for the manufacture of hydroquinone by catalytic dehydrogenation of cyclohexanedione-(1,4) in the liquid phase.

Hydroquinone is used as photographic developer, polymerization inhibitor and as intermediate product for the synthesis of dyestuffs.

Hydroquinone has formerly been produced generally by reduction of p-benzoquinone with iron. The starting product p-benzoquinone is obtained, for example, by oxidation of aniline sulfate with manganese dioxide. The processes involved are quite cumbersome and contaminate the waste water considerably, the short supply of the aromatic starting products being another drawback of these processes.

Good yields of cyclohexanedione-(1,4) may however be obtained from an aliphatic compound, namely succinic acid diethyl ester, with succinylosuccinic acid ester (2,5-dicarbethoxy-1,4-cyclohexanedione) as the intermediate stage. It may furthermore be obtained by oxidation of cyclohexanone.

A process has now been found for the manufacture of hydroquinone, which comprises that cyclohexanedione-(1,4) is added to a dehydrogenation mixture composed of a solvent and of a catalyst comprising a noble metal of Group VIII of the Periodic Table, under a pressure of from 0.5 to 20 atmospheres and at a temperature of from 160° to 350° C in such a way that the concentration of cyclohexanedione-(1,4) does not surpass 50%, calculated on the weight of the liquid phase.

Especially suitable dehydrogenation catalysts are the noble metals palladium, platinum, ruthenium and rhodium. These catalysts are generally charged on support material, such as, for example, carbon, aluminum oxide, silicic acid, magnesium oxide, calcium oxide, titanium oxide and asbestos. Preference is given to the use of palladium on carbon. The most useful concentration of the catalyst varies from 0.02 to 20%, preferably from 0.1 to 10 weight %, calculated on the weight of the support material.

The process may be carried out discontinuously or continuously, at temperatures of from 160° to 350° C. Preferred temperatures are those from 180° to 260° C, since these temperatures achieve a special selectivity combined with a speedy dehydrogenation.

The reaction pressure is from 0.5 to 20 atmospheres and is preferably chosen at such a level that the liquid phase is maintained.

The partial pressure of the hydrogen produced upon dehydrogenation is preferably kept low, so that the equilibrium is shifted in favor of dehydrogenation and that a hydrogenation or hydrogenolysis of the starting compounds and the final products is avoided. This low hydrogen partial pressure may be attained by purging the reaction system with an inert gas such as nitrogen or carbon dioxide.

Suitable solvents are aliphatic or aromatic ethers, for example diphenyl ether; hydrocarbons, such as benzene, toluene, xylene, pseudocumene, naphthalene, biphenyl, tetralene, decalene; ketones, such as acetone, diethyl ketone, methylethyl ketone or methylisobutyl ketone, and also acid amides, such as dimethylformamide or N-methyl pyrrolidone, alcohols, phenols and water. Preferred solvents are aliphatic ethers, for example, the polyglycol dialkyl ethers, such as diethylene glycol dialkyl ether, triethylene glycol dialkyl ether, or tetraethylene glycol dialkyl ethers which generally have alkyl groups with up to 6 carbon atoms. Especially preferred are the polyglycol dimethyl ethers and the polyglycol diethyl ethers. The polyglycol dialkyl ethers have the advantage that they boil under atmospheric pressure within the preferred temperature range of from 180° to 260°, a fact which is particularly advantageous for the process since it allows for operation under normal pressure and since the dehydrogenation is carried out very rapidly and at a high degree of selectivity under reflux conditions. The efficiency of the process is enhanced by vigorous agitation of the reaction mixture for as long as it is contacting the catalyst.

An embodiment which proved to be especially favorable, carrying out the reaction discontinuously, was adding under reflux conditions the cyclohexanedione, dissolved in an easily volatile solvent, such as acetone, isopropanol, methanol or water, to the dehydrogenation mixture composed of suspended catalyst and polyglycol ether as solvent. The solvent for the cyclohexane dione is distilled off the reaction mixture via a descending condensor. The hydrogen formed in the reaction contributes additionally to a thorough mixing. After completion of the reaction the reaction mixture is filtered off the catalyst and the hydroquinone is obtained in its pure state by distillation of the filtrate. When the reaction is carried out continuously, a solution of cyclohexanedione-(1,4) in the same solvent used for suspending the catalyst is generally introduced continuously into the dehydrogenation reactor via a preheating device, while at the same time a corresponding quantity of the reaction mixture containing the hydroquinone is discharged. During this operation, the catalyst is either retained in the reactor by means of a frit or after separation, for example by means of a hydrocyclone, fed back into the reactor. After having separated the solvent from the hydroquinone by distillation, the solvent is re-used for dissolving again cyclohexanedione to be dehydrogenated. The process according to the invention may be carried out either with a fixed-bed catalyst or with a catalyst which is maintained suspended in the reaction solution by agitating vigorously.

In the case of using a fixed-bed catalyst, a catalyst particle size of from 0.5 to 10 mm, preferably of from 2 to 5 mm, is recommended. Larger particles impede the efficiency of the catalyst, whilst smaller particles may lead to catalyst losses and to baking of the catalyst bed.

When the process is carried out with a supported catalyst which is suspended in the reaction medium, the catalyst particle size is generally from 0.01 to 5 mm, preferably from 0.05 to 1 mm. The drawback of smaller particles consists in the difficulty of separating them from the reaction solution. Larger particles, however, are difficult to maintain in suspension and cause an inferior dehydrogenation speed. Depending on the nature of the liquid and of the catalyst, the suspension may contain from 0.1 to 40 parts by weight of supported catalyst per 100 parts by weight of the liquid. A preferred proportion is an amount of from 1 to 30 parts by weight of supported catalyst per 100 parts by weight of solvent.

The process according to the invention has the advantage that the dehydrogenation takes place immediately upon introduction of the cyclohexanedione-(1,4) into the dehydrogenation mixture, so that the rather unstable cyclohexane dione is converted immediately to hydroquinone which is stable under the dehydrogenation conditions.

This effect could not be anticipated, since one skilled in the art had to expect the hydroquinone rather to dehydrogenate further to yield p-quinone and that the latter would continue reacting with hydroquinone to yield quinhydrone.

The following examples illustrate the invention:

EXAMPLE 1

A mixture of 50 ml of polyglycol ethers (90% of triethylene glycol diethyl ether 10% of diethylene glycol diethyl ether and tetraethylene glycol diethyl ether) and 1 g of dehydrogenation catalyst (0.1 g of Pd on 0.9 g of carbon) were heated to 220° C while agitating and purging with nitrogen in a 100 ml three-necked flask equipped with thermometer, agitator, dropping funnel and descending condensor (Claisen-bridge). A solution of 6.0 g of cyclohexanedione-(1,4) in 45 ml of isopropanol was then added continuously within one hour, the temperature of the reaction mixture being maintained meanwhile at 215° C. The isopropanol added was distilled off immediately via the Claisen-bridge. During the addition of cyclohexanedione 1250 ml of hydrogen were formed. After completion of the addition, the contents of the distillation flask were cooled while purging with nitrogen and the catalyst was suctioned off. The filtrate was analyzed by gas chromatography and showed 5.4 g of hydroquinone (91.5% of the theoretical yield). Hydroquinone was obtained from the filtrate by removing the polyglycol ether by means of distillation in vacuo (boiling point from 130° to 140° C under 15 mm of Hg).

EXAMPLE 2

The test operation was the same as in example 1, differing however in that N-methyl-pyrrolidone was charged as solvent for the dehydrogenation. The reaction temperature was from 180° to 185° C. 1210 ml of hydrogen were formed. The gas chromatographic analysis showed 5.3 g (90% of the theoretical yield) of hydroquinone.

What is claimed is:

1. A process for the manufacture of hydroquinone which comprises contacting cyclohexanedione-(1,4) with a solvent selected from the group consisting of polyglycol dialkyl ethers, wherein said alkyl contains up to 6 carbon atoms and a catalyst selected from the group consisting of the noble metals of Group VIII of the Periodic Table, at a pressure from about 0.5 to about 20 atmospheres and a temperature of from about 160° to 350° C, the amount of cyclohexanedione-(1,4) not being in excess of 50%, calculated on the weight of the liquid phase.

2. The process as defined in claim 1, wherein the solvent is methyl-pyrrolidone.

3. A process for the manufacture of hydroquinone which comprises contacting cyclohexanedione-(1,4) with a catalyst selected from the group consisting of palladium, platinum, ruthenium and rhodium, in a liquid phase, in a solvent selected from the group consisting of diethylene glycol dialkyl ether, triethylene glycol dialkyl ether, tetraethylene glycol dialkyl ether, said alkyl having up to 6 carbon atoms, and mixtures thereof, at a temperature of about 160° to 350° C and a pressure of about 0.5 to 20 atmospheres and wherein the amount of cyclohexanedione-(1,4) is not in excess of 50%, calculated on the weight of said liquid phase.

4. The process as defined in claim 3, wherein the temperature is from about 180° to about 260° C.

5. The process as defined in claim 3, wherein the metal is palladium.

6. The process as defined in claim 3, wherein the solvent is a mixture of triethylene glycol diethyl ether, diethylene glycol diethyl ether and tetraethylene glycol diethyl ether.

7. The process of claim 3 wherein said solvent is a member selected from the group of polyglycol dimethyl ethers and polyglycol diethyl ethers.

8. The process of claim 3 wherein said catalyst is carried by a support which is a member selected from the group consisting of carbon, aluminum oxide, silicic acid, magnesium oxide, calcium oxide, titanium oxide and asbestos.

* * * * *